United States Patent [19]
Aoki et al.

[11] Patent Number: 5,383,461
[45] Date of Patent: Jan. 24, 1995

[54] ULTRASONIC DIAGNOSTIC SYSTEM

[75] Inventors: Seiji Aoki; Ryuichi Katou; Yasuhiro Nakamura, all of Yokohama, Japan

[73] Assignee: Matsushita Electric Industrial Co., Ltd., Osaka, Japan

[21] Appl. No.: 151,803

[22] Filed: Nov. 15, 1993

[30] Foreign Application Priority Data

Nov. 25, 1992 [JP] Japan .................. 4-314807

[51] Int. Cl.$^6$ .............................................. A61B 8/00
[52] U.S. Cl. .................................................. 128/660.07
[58] Field of Search ............... 128/660.07, 661.10, 128/660.05, 660.04, 916

[56] References Cited

U.S. PATENT DOCUMENTS

| 4,747,411 | 5/1988 | Ledley | 128/916 |
| 4,873,985 | 10/1989 | Nakajima | 128/661.10 |
| 5,211,169 | 5/1993 | Freeland | 128/661.10 |
| 5,261,404 | 11/1993 | Mick et al. | 128/916 |
| 5,282,471 | 2/1994 | Sato | 128/660.07 |

FOREIGN PATENT DOCUMENTS 236305A 2/1990 Japan .................. 128/660.07

Primary Examiner—George Manuel
Attorney, Agent, or Firm—Stevens, Davis, Miller & Mosher

[57] ABSTRACT

An extended frame memory is provided in parallel with a frame memory, and tomographic images having a number required for computing the cubage of a part to be ultrasonically scanned are stored in the extended frame memory. Thereafter, the thus stored tomographic images are successively read out, and sectional areas are computed from the stored tomographic images. Then, the cubage of the part to be ultrasonically scanned of an examinee is calculated from the thus computed sectional areas. The computation of the cubage is conducted after the tomographic images having a number required for the computation of the cubage are stored in the extended frame memory, thereby it is possible to reduce the burden to the examinee.

6 Claims, 7 Drawing Sheets

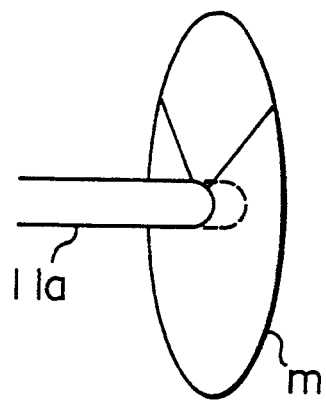
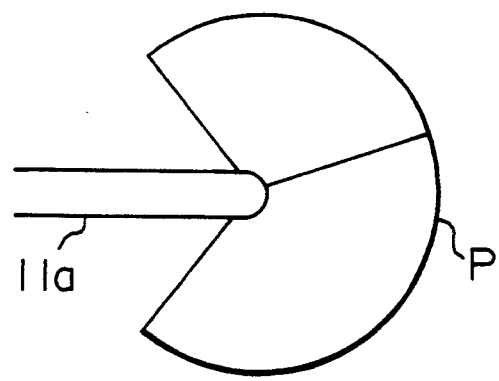
FIG. 3a  FIG. 3b
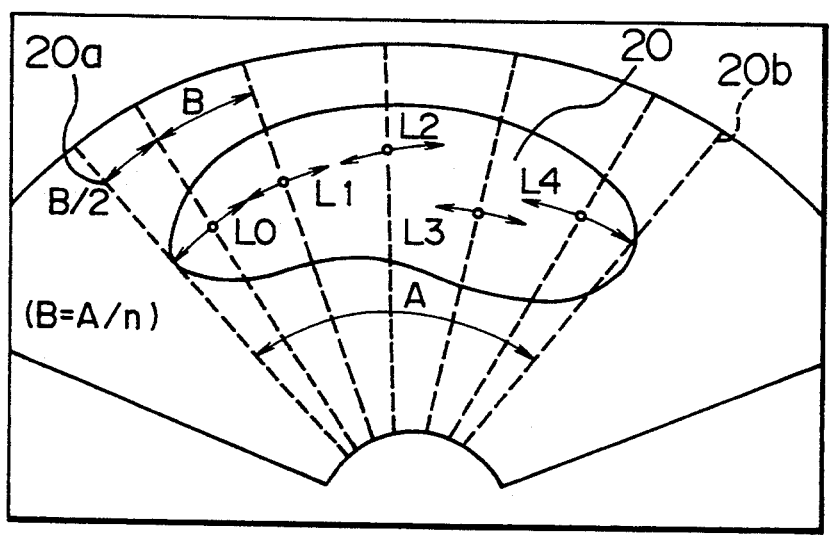
FIG. 4

FIG. 10a

| X→ | | | | | | | | | | | | |
|---|---|---|---|---|---|---|---|---|---|---|---|---|
| 0 | 1 | 0 | 1 | 1 | 0 | 2 | 0 | 0 | 0 | 1 | 1 | 0 |
| 0 | 0 | 1 | 1 | 1 | 0 | 0 | 0 | 2 | 1 | 1 | 0 | 0 |
| 0 | 2 | 1 | 1 | 0 | 90 | 85 | 99 | 80 | 89 | 0 | 0 | 1 |
| 1 | 0 | 0 | 93 | 82 | 82 | 86 | 89 | 90 | 96 | 1 | 0 | 0 |
| 0 | 1 | 97 | 88 | 83 | 92 | 82 | 81 | 96 | 98 | 92 | 1 | 0 |
| 1 | 0 | 89 | 89 | 96 | 92 | 86 | 78 | 75 | 89 | 93 | 1 | 0 |
| 0 | 1 | 80 | 78 | 77 | 85 | 76 | 72 | 78 | 91 | 80 | 0 | 0 |
| 0 | 1 | 81 | 79 | 85 | 78 | 92 | 89 | 70 | 96 | 85 | 0 | 1 |
| 2 | 0 | 97 | 70 | 88 | 74 | 78 | 78 | 90 | 93 | 93 | 0 | 0 |
| 0 | 0 | 1 | 93 | 75 | 89 | 78 | 70 | 85 | 97 | 1 | 0 | 0 |
| 0 | 2 | 1 | 96 | 88 | 97 | 86 | 85 | 88 | 2 | 0 | 0 | 1 |
| 1 | 0 | 0 | 1 | 2 | 0 | 0 | 1 | 0 | 2 | 1 | 0 | 0 |

| X→ | | | | | | | | | | | | |
|---|---|---|---|---|---|---|---|---|---|---|---|---|
| 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 |
| 0 | 0 | 0 | 0 | 0 | 1 | 1 | 1 | 1 | 1 | 0 | 0 | 0 |
| 0 | 0 | 0 | 1 | 1 | 1 | 1 | 1 | 1 | 1 | 0 | 0 | 0 |
| 0 | 0 | 1 | 1 | 1 | 1 | 1 | 1 | 1 | 1 | 1 | 0 | 0 |
| 0 | 0 | 1 | 1 | 1 | 1 | 1 | 1 | 1 | 1 | 1 | 0 | 0 |
| 0 | 0 | 1 | 1 | 1 | 1 | 1 | 1 | 1 | 1 | 1 | 0 | 0 |
| 0 | 0 | 1 | 1 | 1 | 1 | 1 | 1 | 1 | 1 | 1 | 0 | 0 |
| 0 | 0 | 1 | 1 | 1 | 1 | 1 | 1 | 1 | 1 | 1 | 0 | 0 |
| 0 | 0 | 0 | 1 | 1 | 1 | 1 | 1 | 1 | 1 | 0 | 0 | 0 |
| 0 | 0 | 0 | 1 | 1 | 1 | 1 | 1 | 1 | 0 | 0 | 0 | 0 |
| 0 | 0 | 0 | 0 | 0 | 0 | 0 | 0 | 0 | 0 | 0 | 0 | 0 |

(Y ↓)

ULTRASONIC DIAGNOSTIC SYSTEM

BACKGROUND OF THE INVENTION

1. Field of the Invention

The present invention relates to an ultrasonic diagnostic system adapted to be used for medical care.

2. Prior Art of the Invention

In FIG. 7 which is a block diagram that shows a conventional ultrasonic diagnostic system for calculating the cubage of a part to be ultrasonically scanned, there are shown a biplane type ultrasonic probe 1 for transmitting and receiving ultrasonic waves, a transmitting part 2 for delivering an ultrasonic signal for transmitting the ultrasonic waves, to the ultrasonic probe 1, a receiving part 3 for processing an ultrasonic signal received by the ultrasonic probe 1, a frame memory 4 for converting the received ultrasonic signal into an image data, a display part 5 for displaying an image and the result of calculation, a control part 6 for controlling several parts in the system, a computing part 7 for calculating the cubage of a part to be examined of an examinee, and an input device for instructing the transmission and receiving of ultrasonic waves, the display of a tomographic image, the calculation of a cubage or the like.

Next, the operation of the conventional diagnostic system will be explained.

FIG. 8 shows the procedure of the operation of the system. Referring to FIG. 8, a cross-section is displayed so as to set a longitudinal section which is required for the calculation of a cubage (Step 1). Next, as to the longitudinal section, an ultrasonic signal is transmitted from the transmitting part 2. The ultrasonic probe 1 receives waves reflected from an examinee, and delivers an ultrasonic signal to the receiving part 3 which therefore processes the signal. Further, the frame memory 4 stores therein one frame of a tomographic image which is then displayed on the display part 5 (step 2).

This tomographic image is traced by manipulating a track ball, and the sectional area thereof is measured by the computing part 7 (step 3). An image plane and the result of calculation are displayed on the display part 5 together with the tomographic image during the tracing of the tomographic image. The above-mentioned steps are repeated by a necessary number of longitudinal sections (step 4). With the repetitions of the above-mentioned steps by the necessary number of longitudinal sections, sectional areas are obtained, from which the computing part 7 calculates a cubage with the use of a cubage calculating method such as a partial quadrature method (step 5).

With the above-mentioned conventional ultrasonic diagnostic system, the sectional areas of the tombgraphic images should be obtained during the scanning with ultrasonic wave in the case of the calculation of a cubage. Accordingly, the examinee has to hold his body stationary on a measuring bed without moving the same during the operation of measuring sectional areas and calculating a cubage, and accordingly, there has been raised a problem of exerting a burden to the examinee.

SUMMARY OF THE INVENTION

The present invention is devised in order to solve the above-mentioned conventional problem, and accordingly, one object of the present invention is to provide an ultrasonic diagnostic system which can eliminate the necessity of both measurements of sectional areas of a part to be ultrasonically scanned and calculation of the cubage thereof during scanning operation so as to reduce the burden to the examinee.

To this end, according to the present invention, the ultrasonic diagnostic system comprises an ultrasonic tomographic plane processing means for obtaining a tomographic image of a part to be ultrasonically scanned of an object to be examined, a memory means for storing therein a plurality of tomographic images delivered from the ultrasonic tomographic plane processing means, a read-out means for reading out an tomographic image from the memory means when it is designated, a computing means for computing the cubage of the part to be ultrasonically scanned, and a display means for displaying a result of the computation of the cubage of the part to be ultrasonically scanned.

With the ultrasonic diagnostic system according to the present invention, in which tomographic image data can be read out from the memory means storing therein the data, at the time when it is desired, and the result of the calculation of the cubage of the part to be ultrasonically scanned obtained from the tomographic image is displayed on the display means, the manipulation of measuring sectional areas from the tomographic image data, and of computing the cubage of the part to be ultrasonically scanned, is not required during the scanning, and accordingly, the time during which an examinee is required to be stationary, can be shortened so as to reduce the burden to the examinee.

Other features and advantages of the present invention will become apparent during the following discussion of the accompanying drawings, wherein:

BRIEF DESCRIPTION OF THE DRAWINGS

FIG. 3a is a view showing a cross-section in a tomographic image obtained by a biplane type ultrasonic probe, in a plane orthogonal to the axis of the tomographic image;

FIG. 3b is a view showing a longitudinal section in a tomographic image obtained by the biplane type ultrasonic probe, in a plane including the axis of the tomographic image;

FIG. 4 is a view illustrating a tomographic image in a cross-section obtained by the biplane type ultrasonic probe;

FIG. 10a is a view illustrating an expanded frame memory in the variant form of the embodiment; and FIG. 10b is a view showing read-out data in the variant form of the embodiment.

DESCRIPTION OF PREFERRED EMBODIMENT OF THE INVENTION

An embodiment of an ultrasonic diagnostic system according to the present invention will be explained in detail with reference to the drawings.

Figure 1:
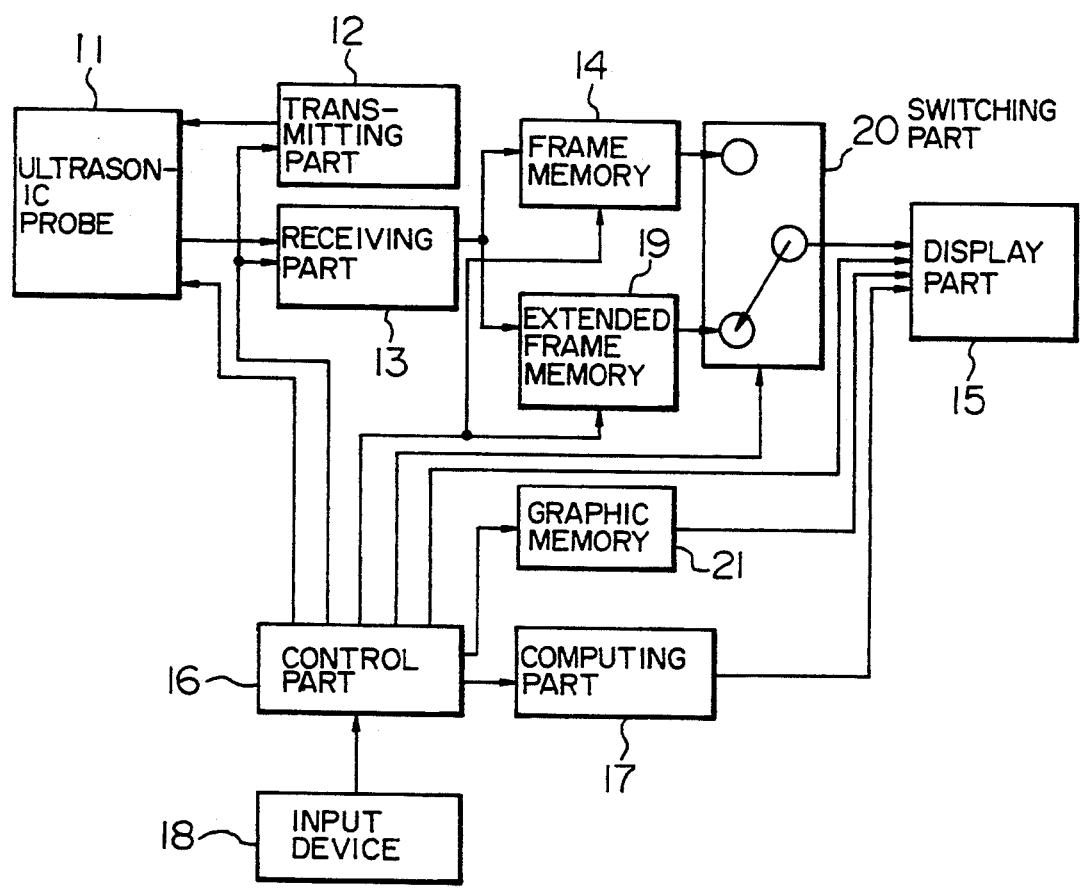
FIG. 1 is a block diagram showing the configuration of an embodiment of an ultrasonic diagnostic system according to the present invention.

Referring to FIG. 1 which shows the arrangement of the embodiment of the ultrasonic diagnostic system according to the present invention, an ultrasonic probe 11 of a biplane type or the like, for transmitting and receiving ultrasonic waves receives a signal for transmitting ultrasonic waves, from a transmitting part 12, and delivers a signal corresponding to ultrasonic waves received thereby to a receiving part 13 for processing the signal. A frame memory 14 converts a signal delivered from the receiving part 13 into an image data.

Further, a display part 15 displays thereon the result of computation and trace data in combination, and a control part 16 controls several parts in the system. A computing part 17 carries out computation of the cubage of a part to be examined in an examinee and the like, and an input device 18 (e.g. using a trackball, mouse, pen, joy-stick, or the like) is used for instructing the transmission and receiving of ultrasonic waves, the display of a tomographic image, the computation of a cubage or the like. An extended frame memory 19 is adapted to store therein a plurality of tomographic images, and a switching part 20 is provided for selecting the frame memory 14 or the extended frame memory 19. A graphic memory 21 stores therein a trace data from an input device 18.

Next, explanation will be made of the operation of the system in this embodiment.

Figure 2:
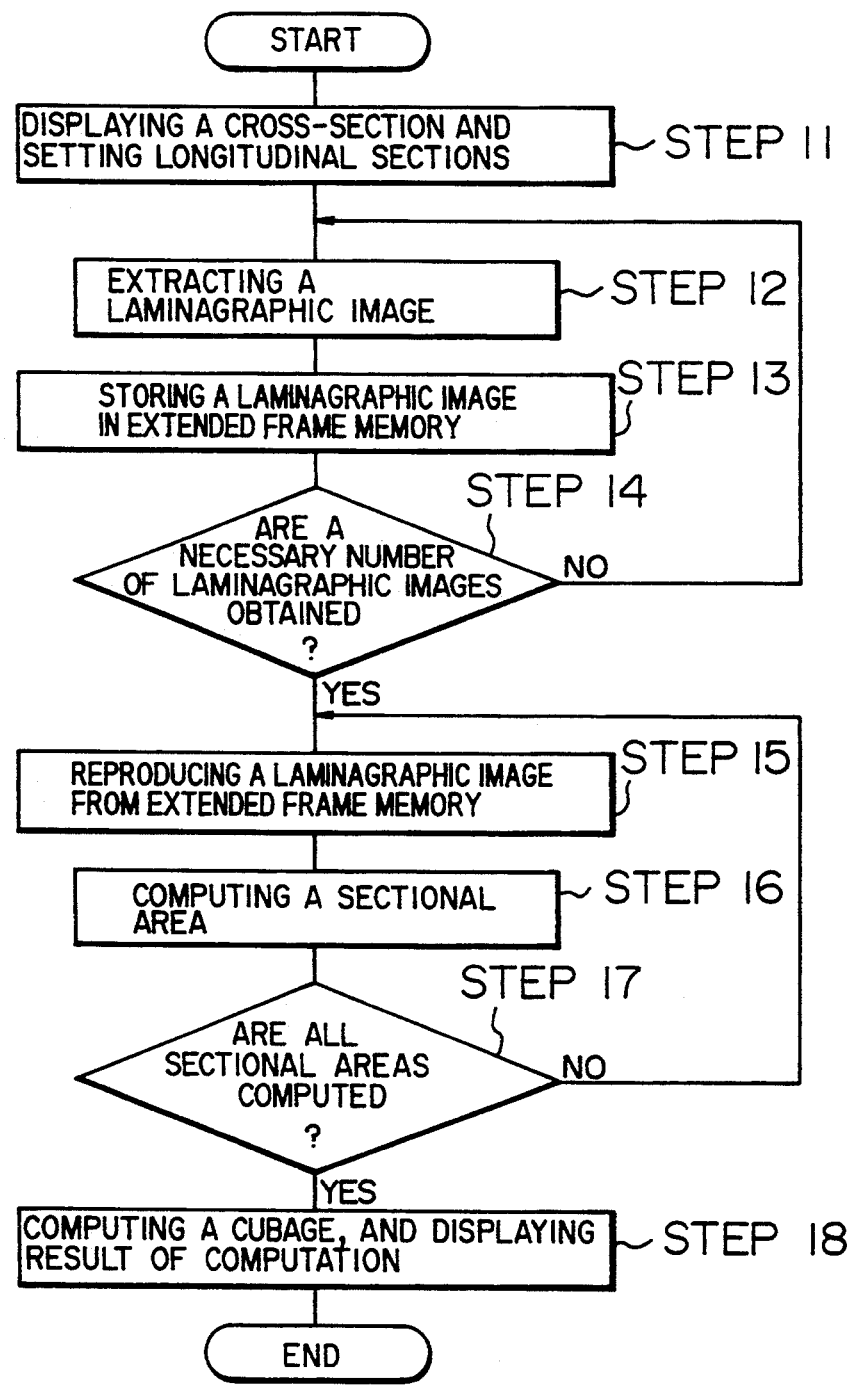
FIG. 2 is a view illustrating a flow-chart for explaining the operation of the embodiment shown FIG. 1.
Figure 5A:
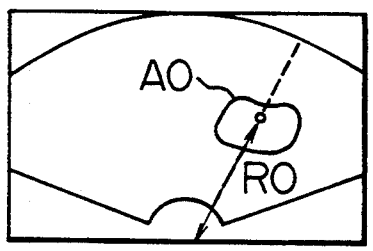
FIG. 5a is a view illustrating the area A0 of a longitudinal section corresponding to the thickness L0 of a part of an object to be measured in the embodiment.
Figure 5D:
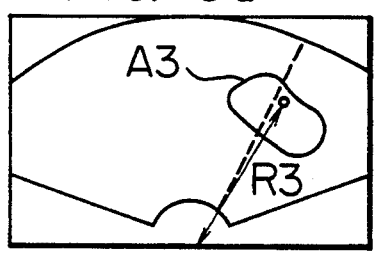
FIG. 5d is a view illustrating the area A3 of a longitudinal section corresponding to the thickness L3 of a part of the object to be measured in the embodiment.
Figure 5B:
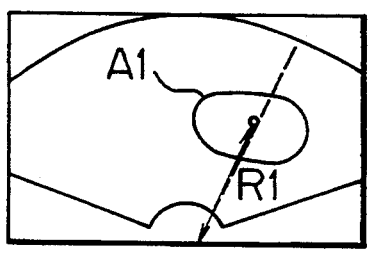
FIG. 5b is a view illustrating the area A1 of a longitudinal section corresponding to the thickness L1 of a part of the object to be measured in the embodiment.
Figure 5E:
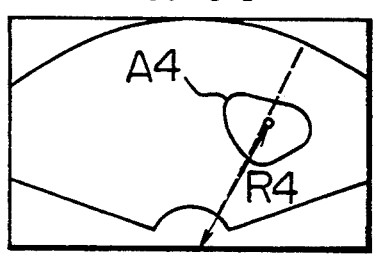
FIG. 5e is a view illustrating the area A4 of a longitudinal section corresponding to the thickness L4 of a part of the object to be measured in the embodiment.
Figure 5C:
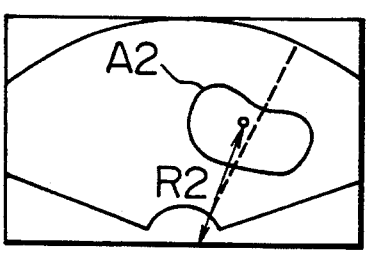
FIG. 5c is a view illustrating the area A2 of a longitudinal section corresponding to the thickness L2 of a part of the object to be measured in the embodiment.

FIG. 2 shows a procedure in the operation of the system. Referring to FIGS. 1 and 2, at first, the input device 18 is manipulated so as to cause the control part 16 to control the switching part 20 in order to select the frame memory 14. Simultaneously, the control part 16 controls the display part 15 so as to display a cross-section which is a plane orthogonal to the axis of the ultrasonic probe 1 as will be detailed hereinbelow with reference to FIG. 3a. Further, longitudinal sections which are required for the computation of a cubage under control by the control part 16 are set (step 11).

Next, as will be hereinbelow detailed with reference to FIG. 3a, the transmitting part 12 delivers an ultrasonic signal to the ultrasonic probe 11 which therefore transmits ultrasonic waves in the longitudinal section. The ultrasonic waves reflected from the examinee is received by the receiving part 13 through the ultrasonic probe 11. A tomographic image corresponding to one frame is stored in the frame memory 14, and then, is displayed as a picture image on the display part 15 (step 12). Simultaneously, the image data of the tomographic image is stored in the extended frame memory 19 (step 13). Steps 11 to 13 are repeated until the extraction of all necessary tomographic images is completed (step 14).

After all tomographic images are stored, the extended memory 19 is selected by means of the switching part 20 so as to successively reproduce the tomographic images from the extended frame memory 19 (step 15). Each of the tomographic images is superposed, on the display part 15, with a trace data delivered from the graphic memory 21 so as to display the tomographic image while the contour of the tomographic image is traced through the input device 18 so as to obtain a trace data thereof. Accordingly, the computing part 17 can compute the sectional area of the tomographic image from the trace data (step 16).

With the repetition of the steps 15 to 16 by the number of the tomographic images stored in the extended frame memory 19, the cubage of the part to be ultrasonically scanned can be computed from the thus obtained sectional areas (steps 17 and 18).

Next, explanation will be made of a method of computing a sectional area from the gradation data of an tomographic image with the use of the computing part 17.

Figure 9:
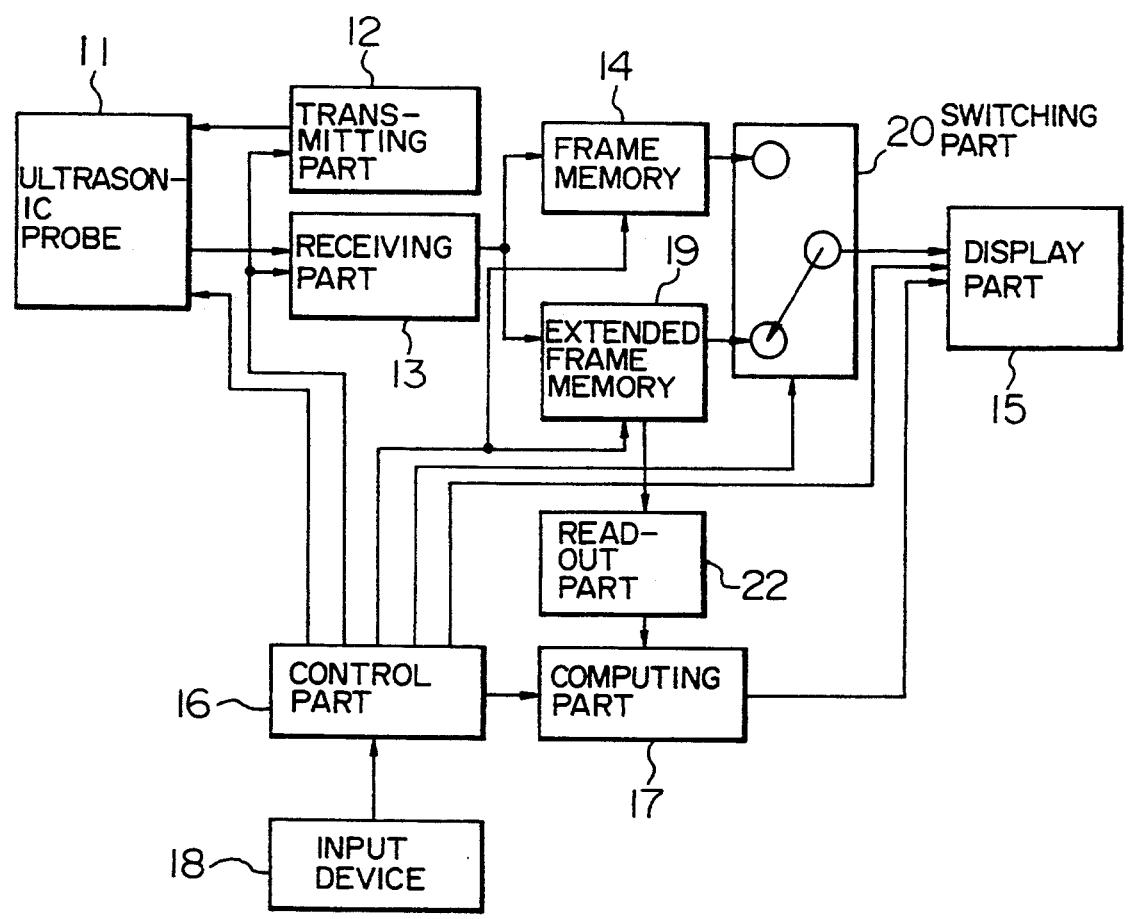
FIG. 9 is a block diagram illustrating a variant form of the embodiment shown in FIG. 1.

Referring to FIG. 9 which shows a configuration used in this method, a read-out part 22 reads out the gradation data of the tomographic image from the extended frame memory 19 so that the computing part 17 can compute the sectional area of the tomographic image. FIG. 10a shows the gradation data of one of the tomographic images stored in the extended frame memory 19, and FIG. 10b shows data which are read out by the readout part 22 in accordance with the gradation data. It is noted here that data having a gradation higher than 50 gradation is regarded as a tomographic image so as to read "1", in this example.

An tomographic image is obtained through the steps 11 to 14, and then, the read-out is made by the read-out part 22 as shown in FIG. 10b. If the area corresponding to one frame in the extended frame memory 19 is known, the sectional area can be obtained from the ratio between the total number of squares of the lattice and the number of squares in each of which data "1" is stored. Accordingly, the computing part 17 computes the sectional area thereof (step 16). In this case, no trace through the input device 18 is required. With the repetitions of steps 15 to 16 by the number of the tomographic images stored in the extended frame memory 19, the cubage of the part to be ultrasonically scanned can be obtained from the thus computed sectional areas.

It is noted that the area corresponding to one frame in the extended frame memory can be obtained by the product of a length in the depthwise direction (Y-axial direction) which is obtained by the product of the sonic velocity of ultrasonic waves and a time by which the ultrasonic waves are received, and a distance in the scanning direction (X-axial direction) which can be obtained by the product of the scanning angle of the beam of the ultrasonic waves and the distance in the depthwise distance.

A partial quadrature can be used for this computation of the cubage. This partial quadrature can precisely obtain the cubage from a plurality of tomographic images. In this case, the cubage of a swelling or an organ is obtained with the use of a biplane type ultrasonic probe 11.

Next explanation will be made of a method of computing the cubage with the use of the biplane type ultrasonic probe 11. With the use of the biplane type ultrasonic probe 11, the cubage can be obtained in a condition such that a tomographic image having a cross-section which m is orthogonal to the axis 11a as shown in FIG. 3a is fixed while the position of the examinee is held to be stationary on an examination bed. Further, with the use of this biplane type ultrasonic probe 11, the cubage can be obtained in a condition such hat a tomographic image having a longitudinal section p in a plane including the axis 11a as shown in FIG. 3b, is fixed while the position of the examinee is held to be stationary on the examination bed.

As shown in FIG. 4, when the left end 20a and the right end 20b of an object to be measured, such as a swelling, which is a tomographic image 20 in a cross-section and a total number (n) of longitudinal sections or the thicknesses L0, L1, L2, L3, L4 of parts in this case, are designated, the longitudinal sections are automatically displayed for every B=A/n (L0 to L4). FIGS. 5a to 5e show the areas A0, A1, A2, A3, A4 of the longitudinal sections corresponding respectively to the thicknesses L0, L1, L2, L3, L4 of the parts. Further, R0, R1, R2, R3 and R4 in FIGS. 5a to 5e, are distances between the gravitational centers of the areas A0, A1, A2, A3, A4 and the rotational center of the ultrasonic probe 11.

Figure 6:
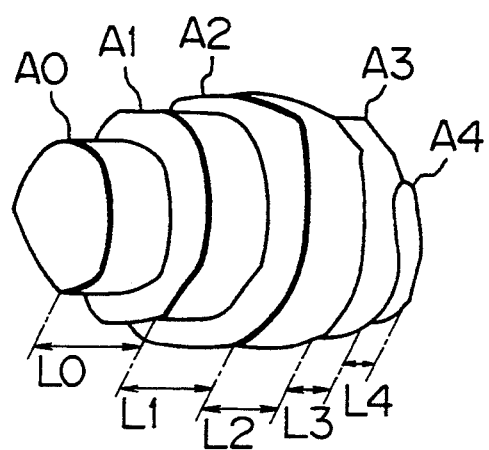
FIG. 6 is a perspective view illustrating the areas and thicknesses of the object to be measured in the tomographic image shown in FIG. 4.
Figure 7:
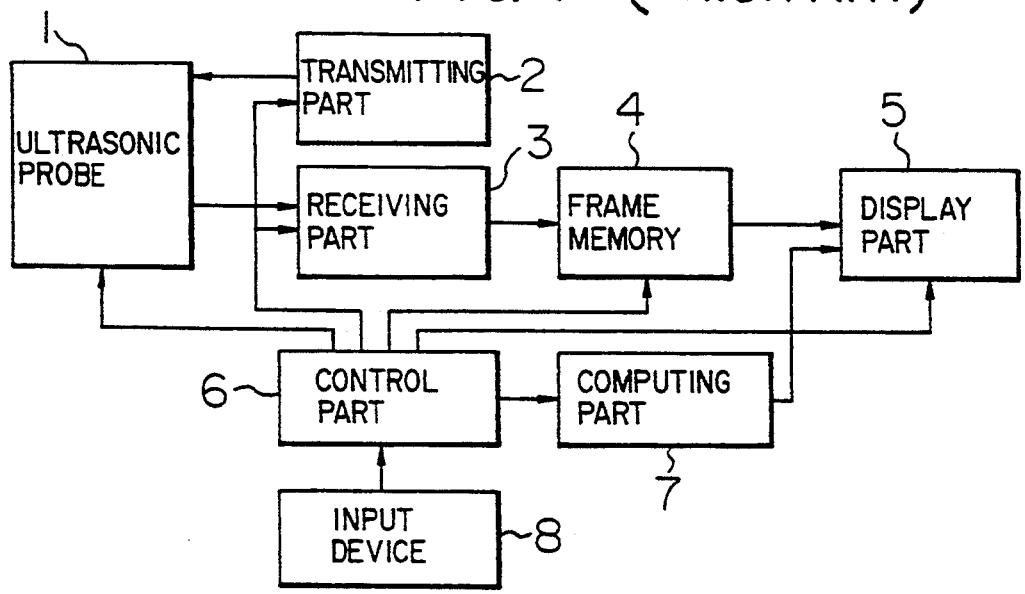
FIG. 7 is a block diagram showing a conventional ultrasonic diagnostic system for computing a part to be ultrasonically scanned.
Figure 8:
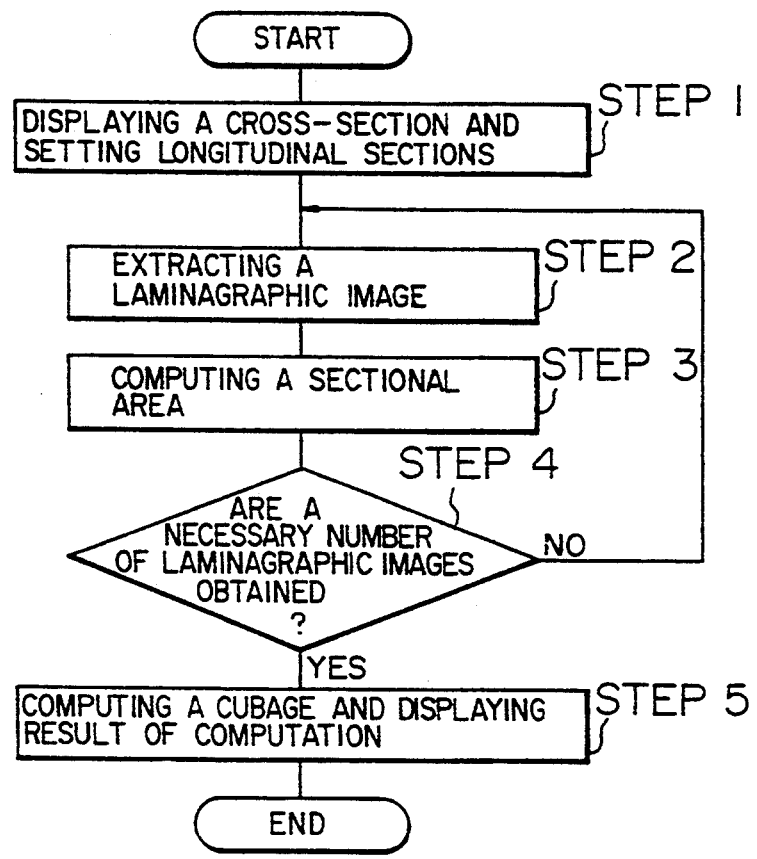
FIG. 8 is a view showing a flow chart for computing the cubage of a part to be ultrasonically scanned.

It is noted that the cubage of the object in the tomographic image 20 in the cross-section shown in FIG. 4 can be obtained with the estimation that each of segments constituting the cubage is planar, having an area Ak (A0 to A4) and a thickness Lk (L1 to L4) as shown in FIG. 6.

The cubages of the tomographic images of the object to be measured are successively obtained by a calliper trace method or the like. The cubage can be computed by the following expression:

$$V = \sum_{k=0}^{n-1} Ak*Lk$$

$$Lk = 2*\pi*Rk*B/360$$

where Rk is the distance between the gravitational center of the area Ak and the rotational center of the ultrasonic probe 11.

As mentioned above, with the use of the biplane type ultrasonic probe 11, when the left and right ends 20a, 20b of the swelling which is the object to be measured in the tomographic image in a cross-section and the number (n, L0 to L4) of longitudinal sections are designated as shown in FIG. 4, a plurality of tomographic images required for the computation of a cubage can be automatically obtained without resetting. Accordingly, the time for obtaining desired tomographic images can be shortened so that the burden to the examinee can be reduced.

As mentioned above, in the ultrasonic diagnostic system according to the present invention, data of tomographic images are read out at designated desired times, and as a result, the cubage of a part to be ultrasonically scanned which is computed from the data of tomographic images is displayed. Accordingly, no manipulation for carrying out the computation of the part to be ultrasonically scanned is required during scanning operation, and it is therefore possible to exhibit an advantage such that the time during which an examinee should be held to be stationary can be shortened, thereby it is possible to reduce the diagnostic burden to the examinee.

What is claimed is:

1. An ultrasonic diagnostic system comprising:
   an ultrasonic probe, having a longitudinal axis, for transmitting and receiving ultrasonic waves in (i) a radial plane orthogonal to said longitudinal axis, to obtain a longitudinal section of an object to be examined and (ii) longitudinal planes, including said longitudinal axis, to obtain crosswise sections of said object to be examined;
   means, operatively associated with said ultrasonic probe, for transmitting signals to said ultrasonic probe so that said ultrasonic probe transmits said ultrasonic waves;
   receiving means, operatively associated with said ultrasonic probe, for receiving signals from said ultrasonic probe corresponding to said ultrasonic waves received by said ultrasonic probe and generating output signals in response thereto;
   a frame memory, operatively associated with said receiving means, for converting said output signals from said receiving means into image data representative of tomographic images in each of said radial and longitudinal planes;
   an extended memory, operatively associated with said frame memory, for successively storing said image data obtained by said frame memory;
   control means, operatively associated with said ultrasonic probe, said frame memory and said extended memory, for controlling said ultrasonic probe to transmit ultrasonic waves in a selected one of said radial plane and said longitudinal planes and for controlling operation of said frame memory and said extended memory;
   input means control means, for inputting instructions to said control means to control said ultrasonic probe to transmit said ultrasonic waves in a selected one of said longitudinal planes; and
   means, operatively associated with said extended memory, for computing areas of said crosswise sections, of said object to be examined, in said tomographic images from said image data stored in said extended memory and for computing a cubage of said object to be examined from the computed areas of said crosswise sections.

2. An ultrasonic diagnosing apparatus as set forth in claim 1, further comprising display means, wherein said output signals from said receiving means are fed into said display means through said frame memory so as to display tomographic images in said radial plane and said longitudinal planes are determined in said radial plane.

3. An ultrasonic diagnosing apparatus as set forth in claim 1, wherein said input means comprises a graphic memory in which said longitudinal planes are stored and said computing means computes said areas of the object to be examined in said tomographic images from said image data which is extracted from the extended memory in accordance with said longitudinal planes stored in said graphic memory.

4. An ultrasonic diagnosing apparatus as set forth in claim 3, further comprising display means, wherein said output signals from said receiving means are fed into said display means through said frame memory so as to display tomographic images in said radial plane and said longitudinal planes are determined in said radial plane.

5. An ultrasonic diagnosing apparatus as set forth in claim 1, further comprising reading means for reading gradation data of said image data stored in said extended memory, wherein said computing means computes contours of said crosswise sections of the object to be examined in said tomographic images from said gradation data and computes the area of said crosswise sections of said objects to be examined from said contours.

6. An ultrasonic diagnosing apparatus as set forth in claim 5, further comprising display means, wherein said output signals from said receiving means are fed into said display means through said frame memory so as to display tomographic images in said radial plane and said longitudinal planes are determined in said radial plane.

* * * * *